US008796236B2

(12) United States Patent
Dodge et al.

(10) Patent No.: US 8,796,236 B2
(45) Date of Patent: Aug. 5, 2014

(54) GENE THERAPY FOR LYSOSOMAL STORAGE DISEASES

(75) Inventors: James Dodge, Framingham, MA (US); Seng Cheng, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 397 days.

(21) Appl. No.: 12/631,336

(22) Filed: Dec. 4, 2009

(65) Prior Publication Data

US 2010/0173979 A1 Jul. 8, 2010

Related U.S. Application Data

(63) Continuation of application No. PCT/US2008/065481, filed on Jun. 2, 2008.

(60) Provisional application No. 60/924,947, filed on Jun. 6, 2007.

(51) Int. Cl.
*A61K 48/00* (2006.01)
*A01N 63/00* (2006.01)

(52) U.S. Cl.
USPC .................... 514/44 R; 424/93.2

(58) Field of Classification Search
USPC .................... 514/44 R; 424/93.2
See application file for complete search history.

(56) References Cited

U.S. PATENT DOCUMENTS

| 2003/0223963 | A1 | 12/2003 | Davidson et al. | |
|---|---|---|---|---|
| 2004/0076613 | A1 | 4/2004 | Mazarakis et al. | |
| 2004/0258666 | A1* | 12/2004 | Passini et al. | 424/93.2 |
| 2006/0171926 | A1 | 8/2006 | Passini et al. | |

FOREIGN PATENT DOCUMENTS

| WO | WO-2005/089462 A2 | 9/2005 |
|---|---|---|
| WO | WO-2006/119458 A9 | 11/2006 |
| WO | WO-2007/095056 A2 | 8/2007 |

OTHER PUBLICATIONS (Eck et al , Goodman & Gilman's The Pharmacological basis of Therapeutics, McGraw-Hill, New York, NY. pp. 77-101, 1996).*
Gorecki et al, (Expert Opin. Emerging Drugs, 6(2): 187-198, 2001).*
Zaiss et al, (Current Gene therapy, vol. 5, p. 323-331, 2005).*
Flotte et al (Current Gene therapy, vol. 5, p. 361-366, 2005).*
Castro et al, (Histl. Histopathol., vol. 16, p. 1225-1238, 2001).*
Lowenstein et al, (Current Opinion in Molecular Therapeutics, vol. 4, No. 4, p. 359-371, 2002).*
Shevtsova et al Exp Physiol., 90(1):53-9, 2005).*
Goncalves (Virology Journal, 2:1-17, 2005).*
Davidson, B.L. et al. (May 2003). "Viral Vectors for Gene Delivery to the Nervous System," *Neuroscience* 4(5):353-364.
Defalco, F. et al. (Mar. 30, 2001). "Virus-Assisted Mapping of Neural Inputs to a Feeding Center in the Hypothalamus," *Science* 291:2608-2613.
Gensert, J.M. et al. (Jul. 1987). "Endogenous Progenitors Remyelinate Demyelinated Axons in the Adult CNS," *Neuron.* 19:197-203.
Gregg, C. et al. (Feb. 21, 2007). "White Matter Plasticity and Enhanced Remyelination in the Material CNS," *The Journal of Neuroscience* 27(8):1812-1823.
Handwerger, S. et al. (Apr. 2000). "The Roles of Placental Growth Hormone and Placental Lactogen in the Regulation of Human Fetal Growth and Development," *Journal of Pediatric endocrinology & Metabolism* 4(13):343-356.
Horinouchi, K. et al. (Jul. 1995). "Acid Sphingomyelinase Deficient Mice: A Model of Types A and B Niemann-Pick Disease," *Nature Genetics* 10(3):288-293.
Kaplitt, M.G. et al. (Oct. 1994). "Long-Term Gene Expression and Phenotypic Correction Using Adeno-Associated Virus Vectors in the Mammalian Brain," *Nature Genetics* 8(2):148-154.
Kaspar, B.K. et al. (Aug. 8, 2003). "Retrograde Viral Delivery of IGF-1 Prolongs Survival in a Mouse ALS Model," *Science* 301:839-842.
Katz, M.L. et al. (1999). "A Mouse Gene Knockout Model for Juvenile Ceriod-Lipofuscinosis (Batten Disease)," *Journal of Neuroscience Research* 57:551-556.
Klein, R.L. et al. (1998). "Neuron-Specific Transduction in the Rat Septohippocampal or Nigrostriatal Pathway by Recombinant Adeno-Associated Virus Vectors," 150:183-194.
Levison, S.W. et al. (1999). "Cycling Cells in the Adult Rat Neocrotex Preferentially Generate Oligodendroglia," *Journal of Neuroscience Research* 57:435-446.
Lindsay, R.M. (Mar.-Apr. 1994). "Neurotrophic Growth Factors and Neurodegenerative Diseases: Therapeutic Potential of the Neurotrophins and Ciliary Neurotrophic Factor," *Neurobiol. Aging* 15(2):249-251.
Lonser, R.R. et al. (2005). "Convection Perfusion of Glucocerebrosidase for Neuronopathic Gauacher's Disease," *Ann. Neurol.* 57:542-548.
Maheshri, N. et al. (Feb. 2006, e-pub. Jan. 22, 2006). "Directed Evolution of Adeno-Associated Virus Yields Enhanced Gene Delivery Vectors," *Nature Biotechnology* 24(2):198-204.
Mandel, R.J. et al. (Jun. 1, 1998). "Characterization of Intrastriatal Recombinant Adeno-Associated Virus-Mediated Gene Transfer of Human Tyrosine Hydroxylase and Human GTP-Cyclohydrolase I in a Rat Model of Parkinson's Disease," *Journal of Neuroscience* 18(11):4271-4284.

(Continued)

*Primary Examiner* — Marcia S Noble
*Assistant Examiner* — Magdalene Sgagias
(74) *Attorney, Agent, or Firm* — Morrison & Foerster LLP (57) ABSTRACT

This disclosure provides methods and compositions for treating lysosomal storage diseases in a subject. In one aspect of the invention, a transgene product is delivered to a subject by administering a recombinant neurotrophic viral vector containing the transgene to the brain. The viral vector delivers the transgene to a region of the brain which is susceptible to infection by the virus and which expresses the encoded recombinant viral gene product. Also provided are compositions for delivery of a transgene product to a subject by administering a recombinant neurotrophic viral vector containing the transgene to the subject's brain. The transgene product may be any that is deficient in a lysosomal storage disease.

7 Claims, 5 Drawing Sheets

(56) References Cited

OTHER PUBLICATIONS

Matsushita, M. et al. (1990). "Afferents to the Cerebellar Nuclei From the Cervical Enlargement in the Rat, as Demonstrated With the *Phaseolus vulgaris* Leucoagglutinin Method *Neuroscience Letters*," 113:253-259.

Menn, B. et al. (Jul. 26, 2006). "Origin of Oligodendrocytes in the Subventricular Zone of the Adult Brain," *The Journal of Neuroscience* 26(30):7907-7918.

Menon, K.P. et al. (1992). "Architecture of the Caine *IDUA* Gene and Mutation Underlying Canine Mucopolysaccharidosis I," *Genomics* 14:763-768.

Miyazaki, J-I. et al. (1989). "Expression Vector System Bases on the Chicken β-Actin Promoter Directs Efficient Production of Interleukin-5," *Gene* 79:269-277.

Muenzer, J. et al. (2002). "Enzyme Replacement Therapy in Mucopolysaccharidosis Type II (Hunter Syndrome): A Preliminary Report," *Acat Paediatr. Supp.* 439:98-99.

Muzyczka, N. (1992). Use of Adeno-Associated Virus as a General Transduction Vector for Mammalian Cells, *Current Topics in Microbiology and Immunology* 158:92-129.

Otterbach, B. et al. (Jun. 30, 1985). "Acid Sphingomyelinase-Deficient Mice Mimic the Neurovisceral Form of Human Lysosomal Storage Disease (niemann-Pick Disease)," *Cell* 81:1053-1061.

Neufeld, E.F. et al. (Jul. 10, 1970). "Inborn Errors of Mucopolysaccharide Metabolism," *Science* 169:141-146.

Polito, A. et al. (2005, e-pub. Jun. 9, 2005). "NG2-Expressing Cells as Oligodendrocyte Progenitors in the Normal and Demyelinated Adult Central Nervous System," *J. Anal.* 207:707-716.

Raben, R. et al. (2003). "Enzyme Replacement Therapy in the House Model of Pompe Disease," *Molecular Genetics and Metabolism* 80:159-169.

Ralph, G.S. et al. (Apr. 2005, e-pub. Mar. 13, 2005). "Silencing Mutant SOD1 Using RNAi Protects Against Neurodegeneration and Extends Survival in an ALS Model," *Nature Medicine* 11(4):429-433.

Rauol, C. et al. (Apr. 2003, e-pub. Mar. 13, 2005). "Lentiviral-Mediated Silencing of SOD1 Through RNA Interference Retards Disease Onset and Progression in a Mouse Model of ALS," *Nature Medicine* 11(4):423-428.

Soudais, C. et al. (Oct. 2004, e-pub. Aug. 17, 2001). "Preferential Transduction of Neurons by Canine Adenovirus Vectors and Their Efficient Retrograde Transport in Vivo," *FASEB J.* 15(12):2283-2285.

Xu, R. et al. (2001). "Quantitative Comparison of Expression With Adeno-Associated Virsu (AAV-2) Brain-Specific Gene Cassettes," *Gene Therapy* 8:1323-1332.

Ye, X. et al. (Jan. 1, 1999). "Regulated Delivery of Therapeutic Proteins After in Vivo Somatic Cell Gene Transfer," *Science* 283:88-91.

International Search Report mailed on Sep. 11, 2008, for PCT Application No. PCT/US2008/065481, one page.

Written Opinion mailed on Sep. 11, 2008, for PCT Application No. PCT/US2008/065481, six pages.

Enquist, I.B. et al. (Oct. 30, 2007). "Murine Models of Acute Neuronopathic Gaucher Disease," *PNAS* 104(44):17483-17488.

Karolewski, B.A. et al. (Jul. 2006, e-pub, Apr. 19, 2006). "Genetic Correction of the Fetal Brain increases the Lifespan of Mice with the Severe Multisystemic Disease Mucopolysaccharidosis Type VII," *Molecular Therapy* 14(1):14-24.

Li, S-H. et al. (2006). "Intra-Ventricular infusion of rAAV1-EGFP Resulted in Transduction in Multiple Regions of Adult Rat Brain: A comparative study with rAAV2 and rAAV5 vectors," *Brain Research* 1122:1-9.

Liu, G. et al. (Oct. 12, 2005). Functional Correction of CNS Phenotypes in a Lysosomal Storage Disease Model Using Adeno-Associated Virus Type 4 Vectors, *The Journal of Neuroscience* 25(41):9321-9327.

McPhee, S.W.J. et al. (2006, e-pub. Mar. 13, 2006). "Immune Responses to AAV in a Phase I Study for Canavan Disease," *The Journal of Gene Medicine* 8:577-588.

Sands, M.S. et al. (May 2006, e-pub. Mar. 20, 2006). "Gene Therapy for Lysosomal Storage Diseases," *Molecular Therapy* 13(5):839-849.

\* cited by examiner

SEQUENCE LISTING

```
<160> NUMBER OF SEQ ID NOS: 2

<210> SEQ ID NO 1
<211> LENGTH: 153
<212> TYPE: PRT
<213> ORGANISM: Homo sapiens
```

<400> SEQUENCE: 1

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
        130                 135                 140

Ser Ala Gly Asn Lys Asn Tyr Arg Met
145                 150

<210> SEQ ID NO 2
<211> LENGTH: 195
<212> TYPE: PRT
<213> ORGANISM: Homo sapiens

<400> SEQUENCE: 2

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Tyr Gln Pro Pro Ser Thr Asn Lys Asn Thr
        130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
195

GENE THERAPY FOR LYSOSOMAL STORAGE DISEASES

FIELD OF THE INVENTION

This invention is related to the area of lysosomal storage diseases.

SUMMARY OF THE INVENTION

Gene therapy is an emerging treatment modality for disorders affecting the central nervous system (CNS). CNS gene therapy has been facilitated by the development of viral vectors capable of effectively infecting post-mitotic neurons. The central nervous system is made up of the spinal cord and the brain. The spinal cord conducts sensory information from the peripheral nervous system to the brain and conducts motor information from the brain to various effectors. For a review of viral vectors for gene delivery to the central nervous system, see Davidson et al. (2003) Nature Rev. 4:353-364.

Adeno-associated virus (AAV) vectors are considered useful for CNS gene therapy because they have a favorable toxicity and immunogenicity profile, are able to transduce neuronal cells, and are able to mediate long-term expression in the CNS (Kaplitt et al. (1994) Nat. Genet. 8:148-154; Bartlett et al. (1998) Hum. Gene Ther. 9:1181-1186; and Passini et al. (2002) J. Neurosci. 22:6437-6446).

One useful property of AAV vectors lies in the ability of some AAV vectors to undergo retrograde and/or anterograde transport in neuronal cells. Neurons in one brain region are interconnected by axons to distal brain regions thereby providing a transport system for vector delivery. For example, an AAV vector may be administered at or near the axon terminals of neurons. The neurons internalize the AAV vector and transport it in a retrograde manner along the axon to the cell body. Similar properties of adenovirus, HSV, and pseudorabies virus have been shown to deliver genes to distal structures within the brain (Soudas et al. (2001) FASEB J. 15:2283-2285; Breakefield et al. (1991) New Biol. 3:203-218; and deFalco et al. (2001) Science, 291:2608-2613).

Several groups have reported that the transduction of the brain by AAV serotype 2 (AAV2) is limited to the intracranial injection site (Kaplitt et al. (1994) Nat. Genet. 8:148-154; Passini et al. (2002) J. Neurosci. 22:6437-6446; and Chamberlin et al. (1998) Brain Res. 793:169-175). Recent reports suggest that retrograde axonal transport of neurotrophic viral vectors can also occur in select circuits of the normal rat brain (Kaspar et al. (2002) Mol. Ther. 5:50-56 (AAV vector); Kasper et al. (2003) Science 301:839-842 (lentiviral vector) and Azzouz et al. (2004) Nature 429:413-417 (lentiviral vector). Roaul et al. (2005) Nat. Med. 11(4):423-428 and Ralph et al. (2005) Nat. Med. 11(4):429-433 report that intramuscular injection of lentivirus expressing silencing human Cu/Zn supreoxide dismutase (SOD1) interfering RNA retarded disease onset of amyotrophic lateral sclerosis (ALS) in a therapeutically relevant rodent model of ALS.

Cells transduced by AAV vectors may express a therapeutic transgene product, such as an enzyme to mediate beneficial effects intracellularly. These cells may also secrete the therapeutic transgene product, which may be subsequently taken up by distal cells where it may mediate its beneficial effects. This process has been described as cross-correction (Neufeld et al. (1970) Science 169:141-146).

A group of metabolic disorders known as lysosomal storage diseases (LSD) includes over forty genetic disorders, many of which involve genetic defects in various lysosomal hydrolases. Representative lysosomal storage diseases and the associated defective enzymes are listed in Table 1.

TABLE 1

| Lysosomal storage disease | Defective enzyme |
|---|---|
| Aspartylglucosaminuria | Aspartylglucosaminidase |
| Fabry | alpha.-Galactosidase A |
| Infantile Batten Disease* (CNL1) | Palmitoyl Protein Thioesterase |
| Classic Late Infantile Batten Disease* (CNL2) | Tripeptidyl Peptidase |
| Juvenile Batten Disease* (CNL3) | Lysosomal Transmembrane Protein |
| Batten, other forms* (CNL4-CNL8) | Multiple gene products |
| Cystinosis | Cysteine transporter |
| Farber | Acid ceramidase |
| Fucosidosis | Acid .alpha.-L-fucosidase |
| Galactosidosialidosis | Protective protein/cathepsin A |
| Gaucher types 1, 2*, and 3* | Acid .beta.-glucosidase |
| G.sub.M1 gangliosidosis* | Acid .beta.-galactosidase |
| Hunter* | Iduronate-2-sulfatase |
| Hurler-Scheie* | alpha.-L-Iduronidase |
| Krabbe* | Galactocerebrosidase. |
| alpha.-Mannosidosis* | Acid .alpha.-mannosidase. |
| beta.-Mannosidosis* | Acid .beta.-mannosidase |
| Maroteaux-Lamy | Arylsulfatase B |
| Metachromatic leukodystrophy* | Arylsulfatase A |
| Morquio A | N-Acetylgalactosamine-6-sulfate |
| Morquio B | Acid .beta.-galactosidase |
| Mucolipidosis II/III* | N-Acetylglucosamine-1-phosphotransferase |
| Niemann-Pick A*, B | Acid sphingomyelinase (aSM) |
| Niemann-Pick C* | NPC-1 |
| Pompe* Acid | .alpha.-glucosidase |
| Sandhoff* | .beta.-Hexosaminidase B |
| Sanfilippo A* | Heparan N-sulfatase |
| Sanfilippo B* | .alpha.-N-Acetylglucosaminidase |
| Sanfilippo C* | Acetyl-CoA: alpha.-glucosaminide N-Acetylglucosamine-6-sulfate |
| Sanfilippo D* | |
| Schindler Disease* | .alpha.-N-Acetylgalactosaminidase |
| Schindler-Kanzaki. | alpha.-N-Acetylgalactosaminidase |
| Sialidosis | .alpha.-Neuramidase |
| Sly* | .beta.-Glucuronidase |
| Tay-Sachs* | .beta.-Hexosaminidase A |
| Wolman* | Acid Lipase |

*CNS involvement

The hallmark feature of LSD is the abnormal accumulation of metabolites in the lysosomes which leads to the formation of large numbers of distended lysosomes in the perikaryon. A major challenge to treating LSD (as opposed to treating a liver-specific enzymopathy) is the need to reverse lysosomal storage pathology in multiple separate tissues. Some LSDs can be effectively treated by intravenous infusion of the missing enzyme, known as enzyme replacement therapy (ERT). For example, Gaucher type 1 patients have only visceral disease and respond favorably to ERT with recombinant glucocerebrosidase (Cerezyme™, Genzyme Corp.). However, patients with metabolic disease that affects the CNS (e.g., type 2 or 3 Gaucher disease) respond partially to intravenous ERT because the replacement enzyme is prevented from entering the brain by the blood brain barrier (BBB). Furthermore, attempts to introduce a replacement enzyme into the brain by direct injection have been limited in part due to enzyme cytotoxicity at high local concentrations and limited parenchymal diffusion rates in the brain (Partridge, Peptide Drug Delivery to the Brain, Raven Press, 1991).

One exemplary LSD, is Niemann-Pick disease type A (NPA). According to UniProtKB/Swiss-Prot entry P17405, defects in the SMPD1 gene, located on chromosome 11, (11p15.4-p15.1), are the cause of Niemann-Pick disease type A (NPA), also referred to as the classical infantile form.

Niemann-Pick disease is a clinically and genetically heterogeneous recessive disorder. It is caused by the accumulation of sphingomyelin and other metabolically related lipids in the lysosomes, resulting in neurodegeneration starting from early life. Patients may show xanthomas, pigmentation, hepatosplenomegaly, lymphadenopathy and mental retardation. Niemann-Pick disease occurs more frequently among individuals of Ashkenazi Jewish ancestry than in the general population. NPA is characterized by very early onset in infancy and a rapidly progressive course leading to death by three years. The acid sphingomyelinase enzyme (aSM) converts sphingomyelin to ceramide. aSM also has phospholipase C activities toward 1,2-diacylglycerolphosphocholine and 1,2-diacylglycerolphosphoglycerol. The enzyme converts Sphingomyelin+$H_2O$→N-acylsphingosine+choline phosphate.

Lysosomal storage diseases can be treated using intraventricular delivery of the enzyme which is etiologically deficient in the disease. The administration can be performed slowly to achieve maximum effect. Effects are seen on both sides of the blood-brain barrier, making this a useful delivery means for lysosomal storage diseases which affect the brain and/or visceral organs.

However, a need still exists for additional compositions and methods to treat lysosomal storage diseases (LSDs) in primate subjects including human patients. This invention satisfies this need and provides related advantages as well.

This invention provides methods and compositions to deliver a transgene to the CNS and/or affected visceral organs of a subject by intraventricular administration of a recombinant neurotrophic viral vector containing a transgene encoding an enzyme which is defective in a lysosomal storage disease. The viral delivery may be under conditions that favor expression of the transgene in ependymal cells.

This invention provides methods and compositions to deliver a transgene to the CNS and/or affected visceral organs of a subject by intraventricular administration of a recombinant neurotrophic viral vector comprising a transgene encoding one or more enzymes selected from the group consisting of Aspartylglucosaminidase, alpha.-Galactosidase A, Palmitoyl Protein Thioesterase, Tripeptidyl Peptidase, Lysosomal Transmembrane Protein, Multiple gene products, Cysteine transporter, Acid ceramidase, Acid .alpha.-L-fucosidase, Protective protein/cathepsin A, Acid .beta.-glucosidase, Acid .beta.-galactosidase, Iduronate-2-sulfatase, alpha.-L-Iduronidase, Galactocerebrosidase., Acid .alpha.-mannosidase, Acid .beta.-mannosidase, Arylsulfatase B, Arylsulfatase A, N-Acetylgalactosamine-6-sulfate, Acid .beta.-galactosidase, N-Acetylglucosamine-1-, Acid sphingomyelinase, NPC-1, .alpha.-glucosidase, .beta.-Hexosaminidase B, Heparan N-sulfatase, .alpha.-N-Acetylglucosaminidase, Acetyl-CoA: alpha.-glucosaminide, N-Acetylglucosamine-6-sulfate, .alpha.-N-Acetylgalactosaminidase, alpha.-N-Acetylgalactosaminidase, .alpha.-Neuramidase, .beta.-Glucuronidase, .beta.-Hexosaminidase A, and Acid Lipase. The viral delivery may be under conditions that favor expression of the transgene in ependymal cells.

In a further aspect, the invention provides compositions and method to ameliorate the symptoms of a lysosomal storage disease in a subject by administering a recombinant neurotrophic viral vector containing the therapeutic transgene to the subject's brain and under conditions that favor expression of the transgene in a therapeutically effective amount.

It is to be understood that both the foregoing general description and the following detailed description are exemplary and explanatory only and are not restrictive of the invention as claimed.

DETAILED DESCRIPTION OF THE INVENTION

In order that the present invention may be more readily understood, certain terms are first defined. Additional definitions are set forth throughout the detailed description.

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a," "an," and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such are known in the art.

The term "transgene" refers to a polynucleotide that is introduced into a cell of and is capable of being transcribed into RNA and optionally, translated and/or expressed under appropriate conditions. In one aspect, it confers a desired property to a cell into which it was introduced, or otherwise leads to a desired therapeutic or diagnostic outcome.

The terms "genome particles (gp)," or "genome equivalents," or "genome copies" (gc), as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

The terms "therapeutic," "therapeutically effective amount," and their cognates refer to that amount of an RNA, DNA or expression product of DNA and/or RNA that results in prevention or delay of onset or amelioration of symptoms of in a subject or an attainment of a desired biological outcome, such as correction of storage pathology, e.g., cellular pathology associated with substrate accumulation in a patient with a lysosomal storage disease. The term "therapeutic correction" refers to that degree of correction which results in prevention or delay of onset or amelioration of symptoms in a subject. The effective amount can be determined by known empirical methods.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provision that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998). Carriers may also comprise artificial cerebrospinal fluid (aCSF).

A "subject," "individual" or "patient" is used interchangeably herein, which refers to a vertebrate, preferably a mammal, more preferably a human. Mammals include, but are not limited to, murines, rats, simians, humans, farm animals, sport animals, and pets.

A "control" is an alternative subject or sample used in an experiment for comparison purpose. A control can be "positive" or "negative." For example, where the purpose of the experiment is to determine a correlation of an altered expression level of a gene with a particular type of pathology, it is generally preferable to use a positive control (a subject or a sample from a subject, carrying such alteration and exhibiting symptoms characteristic of that disease), and a negative control (a subject or a sample from a subject lacking the altered expression and clinical symptom of that disease).

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example one may ameliorate the symptoms of a disease or disorder by making them more bearable.

For identification of structures in the human brain, see, e.g., *The Human Brain: Surface, Three-Dimensional Sectional Anatomy With MRI, and Blood Supply*, 2nd ed., eds. Deuteron et al., Springer Vela, 1999; *Atlas of the Human Brain*, eds. Mai et al., Academic Press; 1997; and *Co-Planar Stereotaxic Atlas of the Human Brain: 3-Dimensional Proportional System: An Approach to Cerebral Imaging*, eds. Tamarack et al., Thyme Medical Pub., 1988. For identification of structures in the mouse brain, see, e.g., *The Mouse Brain in Stereotaxic Coordinates*, 2nd ed., Academic Press, 2000.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads are easy to grow and do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

In one aspect, the invention provides a method to deliver a transgene to the brain of a subject by intraventricular administration of a recombinant neurotrophic viral vector containing a transgene encoding an enzyme which is defective in a LSD. The delivery is under conditions that favor expression of the transgene in ependymal cells.

In another aspect, the invention provides a method of delivering a therapeutic transgene product to the CNS in a mammal afflicted with a lysosomal storage disease, where the transgene may encode a lysosomal enzyme. The transgene can be administered via a neurotrophic virus. The virus can be administered via the ventricles. Ependymal cells may be transduced to express the transgene and secrete the encoded protein product.

In an alternate embodiment, the invention is a method to treat a lysosomal storage disease in a subject by intraventricular administration of a recombinant neurotrophic viral vector containing a therapeutic transgene to the brain of the subject, wherein the transgene is expressed in a therapeutically effective amount in the subject.

This invention also is a method to ameliorate the symptoms of a lysosomal storage disease in a subject by intraventricular administration of a recombinant neurotrophic viral vector containing a therapeutic transgene to the brain, wherein said transgene is expressed in a therapeutically effective amount in the subject.

Suitable neurotrophic viral vectors for the practice of this invention include, but are not limited to adeno-associated viral vectors (AAV), herpes simplex viral vectors (U.S. Pat. No. 5,672,344) and lentiviral vectors.

In the methods of the invention, AAV of any serotype can be used. The serotype of the viral vector used in certain embodiments of the invention is selected from the group consisting from AAV1, AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10(26):3075-81).

AAV vectors are derived from single-stranded (ss) DNA parvoviruses that are nonpathogenic for mammals (reviewed in Muzyscka (1992) Curr. Top. Microb. Immunol., 158:97-129). Briefly, recombinant AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may be maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV4. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888. Additional exemplary AAV vectors are recombinant AAV2/1, AAV2/2, AAV2/5, AAV2/7 and AAV2/8 serotype vectors encoding human protein.

In certain methods of the invention, the vector comprises a transgene operably linked to a promoter. The transgene encodes a biologically active molecule, expression of which in the CNS results in at least partial correction of storage pathology and/or stabilization of disease progression. The transgene may encode one or more of Aspartylglucosaminidase, alpha.-Galactosidase A, Palmitoyl Protein Thioesterase, Tripeptidyl Peptidase, Lysosomal Transmembrane Protein, Multiple gene products, Cysteine transporter, Acid ceramidase, Acid .alpha.-L-fucosidase, Protective protein/cathepsin A, Acid .beta.-glucosidase, Acid .beta.-galactosidase, Iduronate-2-sulfatase, alpha.-L-Iduronidase, Galactocerebrosidase, Acid .alpha.-mannosidase ., Acid .beta.-mannosidase, Arylsulfatase B, Arylsulfatase A, N-Acetylgalactosamine-6-sulfate, Acid .beta.-galactosidase, N-Acetylglucosamine-1-, Acid sphingomyelinase, NPC-1, .alpha.-glucosidase, .beta.-Hexosaminidase B, Heparan N-sulfatase, .alpha.-N-Acetylglucosaminidase, Acetyl-CoA: alpha.-glucosaminide, N-Acetylglucosamine-6-sulfate, .alpha.-N-Acetylgalactosaminidase, alpha.-N-

Acetylgalactosaminidase, .alpha.-Neuramidase, .beta.-Glucuronidase, .beta.-Hexosaminidase A, and Acid Lipase.

One particularly useful enzyme for treating Niemann-Pick A or B is acid sphingomyelinase (aSM), such as that shown in SEQ ID NO: 1. (Residues 1-46 constitute the signal sequence which is cleaved upon secretion.) One particularly useful enzyme for treating Gaucher disease is glucocerebrosidase. One particularly useful enzyme for treating MPS I disease is alpha-L-Iduronidase. One particularly useful enzyme for treating MPS II disease is iduronate-2-sulfatase. One particularly useful enzyme for treating Pompe disease, or glycogen storage disease type II (GSDII), also termed acid maltase deficiency (AMD) is acid alpha-glucosidase. One particularly useful enzyme for treating classic late infantile Batten disease (CLN2) is tripeptidyl peptidase. These enzymes are often recombinant forms of the enzymes produced using methods well-known in the art. In one embodiment, the enzyme is a recombinant human enzyme.

Although a particular amino acid sequence is shown in SEQ ID NO: 1, normal variants in the human population which retain activity can be used as well. Typically these normal variants differ by just one or two residues from the sequence shown in SEQ ID NO: 1. The variants to be used should be at least 95%, 96%, 97%, 98%, or 99% identical to SEQ ID NO: 1. Variants which are associated with disease or reduced activity should not be used. Typically the mature form of the enzyme will be delivered. This will begin with residue 47 as shown in SEQ ID NO: 1. In a similar manner, normal variants in the human population of such LSD enzymes as glucocerebrosidase, alpha-L-Iduronidase, iduronate-2-sulfatase, acid alpha-glucosidase, and tripeptidyl peptidase that which retain enzymatic activity can be used as well.

The populations treated by the methods of the invention include, but are not limited to, patients having or at risk for developing a neurometabolic disorder, e.g., an LSD, such as diseases listed in Table 1, particularly, if such a disease affects the CNS and visceral organs. In an illustrative embodiment, the disease is Niemann-Pick disease, type A, B, or C, Gaucher disease, Mucopolysaccharidoses (MPS), Pompe disease, or Batten disease.

A transgene encoding aSM or other lysosomal hydrolase enzyme can be incorporated into a pharmaceutical composition useful to treat, e.g., inhibit, attenuate, prevent, or ameliorate, a condition characterized by an insufficient level of a lysosomal hydrolase activity. The pharmaceutical composition will be administered to a subject suffering from a lysosomal hydrolase deficiency or someone who is at risk of developing said deficiency. The compositions should contain a therapeutic or prophylactic amount of the transgene encoding an aSM or other lysosomal hydrolase enzyme, in a pharmaceutically-acceptable carrier. The pharmaceutical carrier can be any compatible, non-toxic substance suitable to deliver the polypeptides to the patient. Sterile water, alcohol, fats, and waxes may be used as the carrier. Pharmaceutically-acceptable adjuvants, buffering agents, dispersing agents, and the like, may also be incorporated into the pharmaceutical compositions. The carrier can be combined with the aSM or other lysosomal hydrolase enzyme in any form suitable for administration by intraventricular injection or infusion (also possibly intravenous or intrathecal) or otherwise. Suitable carriers include, for example, physiological saline, bacteriostatic water, Cremophor EL™ (BASF, Parsippany, N.J.) or phosphate buffered saline (PBS), other saline solutions, dextrose solutions, glycerol solutions, water and oils emulsions such as those made with oils of petroleum, animal, vegetable, or synthetic origin (peanut oil, soybean oil, mineral oil, or sesame oil). An artificial CSF can be used as a carrier. The carrier will preferably be sterile and free of pyrogens. The concentration of the transgene encoding aSM or other lysosomal hydrolase enzyme in the pharmaceutical composition can vary widely.

Intracerebroventricular, or intraventricular delivery of a recombinant viral vector may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adults, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infants. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres.

While not wishing to be bound by any theory or mechanism of operation, administration to the CNS of an afflicted subject of a neurotrophic viral vector carrying a transgene encoding a therapeutic product permits transport of the viral vector and/or expressed product via the CSF throughout the CNS and/or to the visceral organs. The CSF empties into the blood via the arachnoid villi and intracranial vascular sinuses, thereby delivering the enzymes and/or the transgenes to the visceral organs that are known to be affected in LSDs. The visceral organs which are often affected in Niemann-Pick disease, for example, are the lungs, spleen, kidney, and liver. The gene therapy provides diminished amounts of substrate in at least the brain and potentially in visceral organs . The reduction in substrate accumulated in the brain, lungs, spleen, kidney, and/or liver may be dramatic. Reductions of greater that 10%, 20%, 30%, 40%, 50%, 60%, 70%, 80%, 90% can be achieved. The reduction achieved is not necessarily uniform from patient to patient or even from organ to organ within a single patient.

The lysosomal storage diseases (LSD) include over forty genetic disorders, many of which involve genetic defects in various lysosomal hydrolases. Representative lysosomal storage diseases and the associated defective enzymes are listed in Table 1.

Gaucher disease results as a consequence of an inherited deficiency of the lysosomal hydrolase glucocerebrosidase (GC), leading to the accumulation of its substrate, glucosylceramide (GL-1), in the lysosomes of histiocytes. The progressive accumulation of GL-1 in tissue macrophages (Gaucher cells) occurs in various tissues. The extent of the accumulation is dependent in part on the genotype. Clinically, three different Gaucher phenotypes are recognized, the non-neuropathic type 1, which is the most common with onset ranging from early childhood to adulthood, and the neuropathic types 2 and 3, presenting in infancy and early childhood, respectively. The primary clinical manifestations common to all forms of Gaucher disease are hepatosplenomegaly, cytopenia, pathological bone fractures and, occasionally, pulmonary failure. A detailed discussion of Gaucher disease may be found in the Online Metabolic & Molecular Bases of Inherited Diseases, Part 16, Chapter 146 and 146.1 (2007). In patients with type 2 and type 3 Gaucher disease in whom there is significant central nervous system involvement, intraventricular delivery of the defective LSD enzyme leads to improved metabolic status of the brain and possibly the affected visceral (non-CNS) organs. Intraventricular delivery of the defective LSD enzyme in subjects with Gaucher type 1 disease leads to improved metabolic status of affected visceral (non-CNS) organs. There are animal models of Gaucher disease, which have derived from mouse models created by targeted disruption of the corresponding mouse gene. For example, a Gaucher mouse model harboring the D409V mutation in the mouse GC locus exists (Xu, Y—H et al. (2003). Am. J. Pathol. 163:2093-2101). The heterozygous mouse, gbaD409V/null, exhibits ☐ 5% of normal GC activity in visceral tissues and develops lipid-engorged macrophages (Gaucher cells) in the liver, spleen, lung and bone marrow by 4 months of age. Other examples of mouse models of Gaucher disease are the models of acute neuronopathic Gaucher disease developed by Enquist et al. 2007 PNAS 104(44): 17483-17488. These mice exhibit close similarity, in both pathological findings and clinical manifestations, to human patients with severe neuronopathic Gaucher disease. Accordingly, all of the models discussed above are suitable systems in which to evaluate the benefits of intraventricular delivery of a viral neurotrophic vector encoding the defective LSD enzyme in subjects with Gaucher disease.

Niemann-Pick disease (NPD) is a lysosomal storage disease and is an inherited neurometabolic disorder characterized by a genetic deficiency in acid sphingomyelinase (aSM; sphingomyelin cholinephosphohydrolase, EC 3.1.3.12). The lack of functional aSM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of aSMKO mice and human patients (Leventhal et al. (2001) J. Biol. Chem., 276:44976-44983; Slotte (1997) Subcell. Biochem., 28:277-293; and Viana et al. (1990) J. Med. Genet., 27:499-504.) A detailed discussion of NPD disease may be found in the Online Metabolic & Molecular Bases of Inherited Diseases, Part 16, Chapter 144 (2007). There are animal models of NPD. For example, aSMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Intraventricular delivery of a transgene encoding the defective LSD enzyme leads to improved metabolic status of the brain and the affected visceral (non-CNS) organs.

Mucopolysaccharidoses (MPS) are a group of lysosomal storage disorders caused by deficiencies of enzymes catalyzing the degradation of glycosaminoglycans (mucopolysaccharides). There are 11 known enzyme deficiencies that give rise to 7 distinct MPS, including MPS I (Hurler, Scheie, and Hurler-Scheie Syndromes) and MPS II (Hunter Syndrome). A detailed discussion of MPS may be found in the Online Metabolic & Molecular Bases of Inherited Diseases, Part 16, Chapter 136 (2007). There are numerous animal models of MPS, which have derived from naturally occurring mutations in dogs, cats, rats, mice, and goats, as well as mouse models created by targeted disruption of the corresponding mouse gene. The biochemical and metabolic features of these animal models are generally quite similar to those found in humans; however, the clinical presentations may be milder. For example, accepted models for MPS I include a murine model [Clark, L A et al., Hum. Mol. Genet. (1997), 6:503] and a canine model [Menon, K P et al., Genomics (1992), 14:763. For example, accepted models for MPS II include a mouse model [Muenzer, J. et al., (2002), Acta Paediatr. Suppl.; 91(439):98-9]. In the MPS that have central nervous system involvement, such as is found in patients with MPS I and MPS II, intraventricular delivery of a transgene encoding the defective LSD enzyme leads to improved metabolic status of the brain and possibly the affected visceral (non-CNS) organs.

Pompe disease, or glycogen storage disease type II (GSDII), also termed acid maltase deficiency (AMD) is an inherited disorder of glycogen metabolism resulting from defects in activity of the lysosomal hydrolase acid alpha-glucosidase in all tissues of affected individuals. The enzyme deficiency results in intralysosomal accumulation of glycogen of normal structure in numerous tissues. The accumulation is most marked in cardiac and skeletal muscle and in hepatic tissues of infants with the generalized disorder. In late-onset GSDII, intralysosomal accumulation of glycogen is virtually limited to skeletal muscle and is of lesser magnitude. Electromyographic abnormalities suggestive of the diagnosis include pseudomyotonic discharges and irritability, but in juvenile- and adult-onset patients, the abnormalities can vary in different muscles. CAT scans can reveal the site(s) of affected muscles. Most patients have elevated blood plasma levels of creatine kinase (CK) and elevations in hepatic enzymes, particularly in adult-onset patients, can be found. There are several naturally occurring animal models of the infantile- and late-onset disease. There is a knockout mouse model [Bijvoet A G et al., Hum. Mol. Genet. (1998); 7:53-62.]. Ameliorative effects of enzyme therapy have been described in knockout mice [Raben, N et al., Mol. Genet. Metab. (2003); 80:159-69] and in a quail model. Intraventricular delivery of a transgene encoding the defective LSD enzyme leads to improved metabolic status of the brain and possibly the affected visceral (non-CNS) organs.

The neuronal ceroid lipofuscinoses (NCL) are a group of neurodegenerative disorders distinguished from other neurodegenerative diseases by the accumulation of autofluorescent material ("aging pigment") in the brain and other tissues. The major clinical features include seizures, psychomotor deterioration, blindness, and premature death. Distinct subgroups of NCL have been recognized that differ in the age of onset of symptoms and the appearance of the storage material by electron microscopy. Three major groups-infantile (INCL), classical late infantile (LINCL), and juvenile (JNCL, also referred to as Batten disease)-are caused by autosomal recessive mutations in the CLN1, CLN2, and CLN3 genes, respectively. The protein products of the CLN1 (palmitoyl-protein thioesterase) and CLN2 (tripeptidyl peptidase or pepinase)

genes are soluble lysosomal enzymes, whereas the CLN3 protein (battenin) is a lysosomal membrane protein, as is (tentatively) the CLN5 protein. The identification of mutations in genes encoding lysosomal proteins in several forms of NCL has led to the recognition of the lipofuscinoses as true lysosomal storage disorders. A detailed discussion of NCL disease may be found in the Online Metabolic & Molecular Bases of Inherited Diseases, Part 16, Chapter 154 (2007). Naturally occurring NCL disorders have been described in the sheep, dog, and mouse models have been derived by targeted disruption of a corresponding mouse gene [see e.g., Katz, M L et al., J. Neurosci. Res. (1999); 57:551-6; Cho, S K et al., Glycobiology (2005); 15:637-48.] Intraventricular delivery of a transgene encoding the defective LSD enzyme leads to improved metabolic status of the brain and possibly the affected visceral (non-CNS) organs.

A detailed discussion of additional lysosomal storage disorders disclosed in Table 1, in which intraventricular delivery of the defective LSD enzyme in the disease, may be found in the Online Metabolic & Molecular Bases of Inherited Diseases, Part 16 (2007).

The level of transgene expression in eukaryotic cells is largely determined by the transcriptional promoter within the transgene expression cassette. Promoters that show long-term activity and are tissue- and even cell-specific are used in some embodiments. Non limiting examples of promoters include, but are not limited to, the cytomegalovirus (CMV) promoter (Kaplitt et al. (1994) Nat. Genet. 8:148-154), CMV/human β3-globin promoter (Mandel et al. (1998) J. Neurosci. 18:4271-4284), GFAP promoter (Xu et al. (2001) Gene Ther. 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277), the β-glucuronidase (GUSB) promoter (Shipley et al. (1991) Genetics 10:1009-1018), and ubiquitin promoters such as those isolated from human ubiquitin A, human ubiquitin B, and human ubiquitin C as described in U.S. Pat. No. 6,667,174. To prolong expression, other regulatory elements may additionally be operably linked to the transgene, such as, e.g., the Woodchuck Hepatitis Virus Post-Regulatory Element (WPRE) (Donello et al. (1998) J. Virol. 72:5085-5092) or the bovine growth hormone (BGH) polyadenylation site.

For some CNS gene therapy applications, it may be necessary to control transcriptional activity. To this end, pharmacological regulation of gene expression with viral vectors can been obtained by including various regulatory elements and drug-responsive promoters as described, for example, in Haberman et al. (1998) Gene Ther. 5:1604-16011; and Ye et al. (1995) Science 283:88-91.

In certain embodiments, the concentration or titer of the vector in the composition is at least: (a) 5, 6, 7, 8, 9, 10, 15, 20, 25, or 50 ($\times 10^{12}$ gp/ml); (b) 5, 6, 7, 8, 9, 10, 15, 20, 25, or 50 ($\times 10^9$ to/ml); or (c) 5, 6, 7, 8, 9, 10, 15, 20, 25, or 50 ($\times 10^{10}$ iu/ml).

In one aspect, the transgene encodes a biologically active molecule, expression of which in the CNS results in at least partial correction of storage pathology and/or stabilization of disease progression. In some embodiments, the therapeutic transgene product is an aSM protein that alleviates and/or prevents the symptoms of Niemann-Pick A and B. See Roaul et al. (2005) Nat. Med. 11(4):423-428 and Ralph et al. (2005) Nat. Med. 11(4):429-433. In other embodiments, transgenes encoding the enzymes defective in other LSD are delivered, as appropriate for the particular patient.

In one aspect when performing these methods, the transgene expresses a therapeutic amount of an enzyme selected from the group consisting of Aspartylglucosaminidase, alpha.-Galactosidase A, Palmitoyl Protein Thioesterase, Tripeptidyl Peptidase, Lysosomal Transmembrane Protein, Multiple gene products, Cysteine transporter, Acid ceramidase, Acid .alpha.-L-fucosidase, Protective protein/cathepsin A, Acid .beta.-glucosidase, or, Acid .beta.-galactosidase, Iduronate-2-sulfatase, alpha.-L-Iduronidase, Galactocerebrosidase ., Acid .alpha.-mannosidase ., Acid .beta.-mannosidase, Arylsulfatase B, Arylsulfatase A, N-Acetylgalactosamine-6-sulfate, Acid .beta.-galactosidase, N-Acetylglucosamine-1-, Acid sphingomyelinase, NPC-1, .alpha.-glucosidase, .beta.-Hexosaminidase B, Heparan N-sulfatase, .alpha.-N-Acetylglucosaminidase, Acetyl-CoA: alpha.-glucosaminide, N-Acetylglucosamine-6-sulfate, .alpha.-N-Acetylgalactosaminidase, alpha.-N-Acetylgalactosaminidase, .alpha.-Neuramidase, .beta.-Glucuronidase, .beta.-Hexosaminidase A, and Acid Lipase.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Stereotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Stereotaxic Coordinates, 2nd ed., Academic Press, 2000.

To deliver the solution or other composition containing the viral vector specifically to a particular region of the central nervous system, such as to a particular ventricle, e.g., to the lateral ventricles or to the fourth ventricle of the brain, it may be administered by stereotaxic microinjection. For example, on the day of surgery, patients will have the stereotaxic frame base fixed in place (screwed into the skull). The brain with stereotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector solution in a pharmaceutically acceptable carrier will then be injected. Additional routes of administration may be used, e.g., superficial cortical application under direct visualization, or other non-stereotaxic application.

One way for delivering the viral vector is to use a pump. Such pumps are commercially available, for example, from Alzet (Cupertino, Calif.) or Medtronic (Minneapolis, Minn.). The pump may be implantable. Another convenient way to administer the vector is to use a cannula or a catheter.

The subject invention provides methods to modulate, correct or reduce symptoms in a subject afflicted with a lysosomal storage disease, by reducing substrate accumulation in the CNS or affected visceral organs. For the purpose of illustration only, the subject may suffer from one or more of Aspartylglucosaminuria, Fabry, Infantile Batten Disease (CNL1), Classic Late Infantile Batten Disease (CNL2), Juvenile Batten Disease (CNL3), Batten, other forms (CNL4-CNL8), Cystinosis, Farber, Fucosidosis, Galactosidosialidosis, Gaucher types 1, 2, and 3, G.sub.M1 gangliosidosis, Hunter, Hurler-Scheie, Krabbe, alpha.-Mannosidosis, beta.-Mannosidosis, Maroteaux-Lamy, Metachromatic leukodystrophy, Morquio A, Morquio B, Mucolipidosis Niemann-Pick A, B, Niemann-Pick C, Pompe Acid, Sandhoff, Sanfilippo A, Sanfilippo B, Sanfilippo C, Sanfilippo D, Schindler Disease, Schindler-Kanzaki Sialidosis, Sly, Tay-Sachs, and Wolman Disease.

If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds. Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

In one aspect, the disclosed methods include administering to the CNS of an afflicted subject a neurotrophic viral vector carrying a transgene encoding a therapeutic product and allowing the transgene to be expressed within the CNS and/or visceral organs at a level sufficient to exert a therapeutic effect as the expressed protein is transported via the CSF throughout the CNS and/or visceral organs. In addition, the vector may comprise a polynucleotide encoding for a biologically active molecule effective to treat the CNS disorder. Such biologically active molecules may comprise peptides including but not limited to native or mutated versions of full-length proteins, native or mutated versions of protein fragments, synthetic polypeptides.

In an illustrative embodiment, the administration is accomplished by direct injection of a high titer vector solution into one or more of the ventricular spaces of the brain, such as the lateral ventricle of a subject or patient. For example, the administration is by direct bolus injection into one or more ventricles of the brain such as the lateral and fourth ventricles.

In some embodiments, the methods comprise administration of a high titer neurotrophic vector carrying a therapeutic transgene so that the transgene product is expressed at a therapeutic level at a first site within the CNS distal to the ultimate site of action of the expressed product. In some embodiments, the viral titer of the composition is at least: (a) 5, 6, 7, 8, 9, 10, 15, 20, 25, or 50 ($\times 10^{12}$ gp/ml); (b) 5, 6, 7, 8, 9, 10, 15, 20, 25, or 50 ($\times 10^{9}$ to/ml); or (c) 5, 6, 7, 8, 9, 10, 15, 20, 25, or 50 ($\times 10^{10}$ iu/ml).

In experimental mice, the total volume of injected AAV solution is for example, between 1 to 20 µl For other mammals, including the human brain, volumes and delivery rates are appropriately scaled. For example, it has been demonstrated that volumes of 150 µl can be safely injected in the primate brain (Janson et al. (2002) Hum. Gene Ther. 13:1391-1412). Treatment may consist of a single injection per target site, or may be repeated in one or more ventricles. Suitable ventricles include the lateral ventricles, third ventricle, and the fourth ventricle. Multiple injection sites can be used. For example, in some embodiments, in addition to the first administration site, a composition containing a viral vector carrying a transgene is administered to another site which can be contralateral or ipsilateral to the first administration site. Injections can be single or multiple, unilateral or bilateral.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Titration of Recombinant Vectors

AAV vector titers are measured according to genome copy number (genome particles per milliliter). Genome particle concentrations are based on Taqman® PCR of the vector DNA as previously reported (Clark et al. (1999) Hum. Gene Ther., 10:1031-1039; Veldwijk et al. (2002) Mol. Ther., 6:272-278).

Vectors carrying an assayable marker gene such as the β-galactosidase (Lac Z) or green fluorescent protein gene (GFP) can be titered using an infectivity assay. Susceptible cells (e.g., HeLa, or COS cells) are transduced with the AAV and an assay is performed to determine gene expression such as staining of β-galactosidase vector-transduced cells with X-gal (5-bromo-4chloro-3-indolyl-β-D-galactopyranoside) or fluorescence microscopy for GFP-transduced cells. For example, the assay is performed as follows: $4 \times 10^4$ HeLa cells are plated in each well of a 24-well culture plate using normal growth media. After attachment, i.e., about 24 hours later, the cells are infected with Ad type 5 at a multiplicity of infection (MOI) of 10 and transduced with serial dilutions of the packaged vector and incubated at 37° C. One to three days later, before extensive cytopathic effects are observed, the appropriate assay is performed on the cells (e.g., X-gal staining or fluorescence microscopy). If a reporter gene such as β-galactosidase is used, the cells are fixed in 2% paraformaldehyde, 0.5% glutaraldehyde and stained for β-galactosidase activity using X-gal. Vector dilutions that give well-separated cells are counted. Each positive cell represents 1 transduction unit (tu) of vector.

Animal Model

ASMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Niemann-Pick disease (NPD) is classified as a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem., 276:44976-44983; Slotte (1997) Subcell. Biochem., 28:277-293; and Viana et al.

(1990) J. Med. Genet., 27:499-504.) Other models for other LSD are discussed above and can be used as is appropriate.

Figure 1:
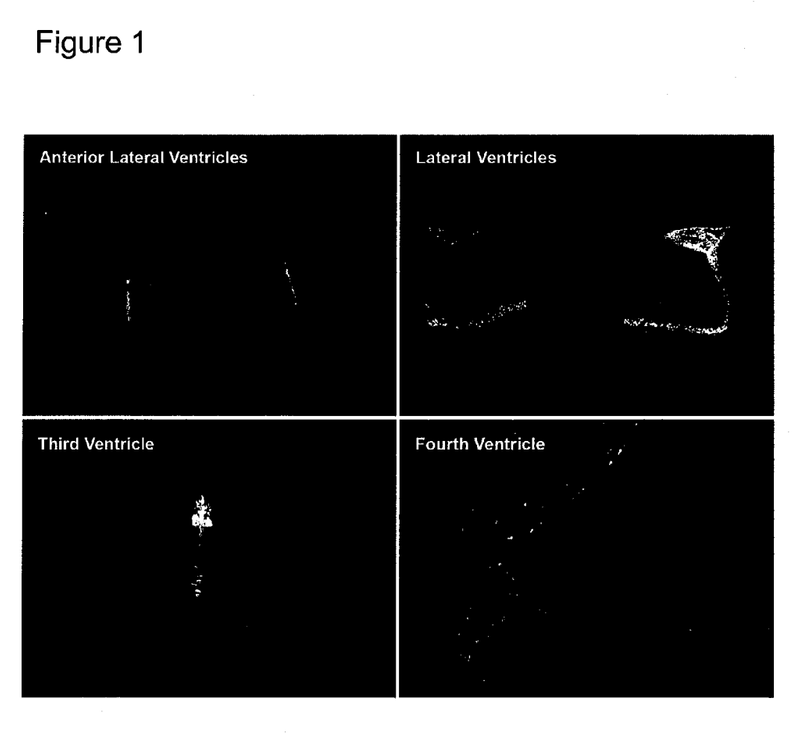
FIG. 1 shows green fluorescent protein (GFP) expression in mice treated with AAV4-GFP. GFP is distributed in the ependymal cell layer of the ventricular system following intraventricular delivery of AAV4-GFP.
Figure 2:
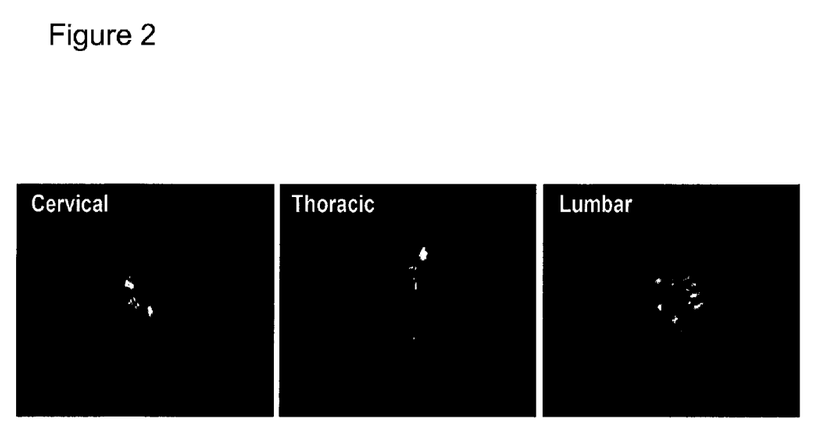
FIG. 2 shows green fluorescent protein (GFP) expression in mice treated with AAV4-GFP. GFP is distributed in the ependymal cell layer of the spinal cord central canal following intraventricular delivery of AAV4-GFP.

Visualization of green fluorescent protein (GFP) expression in mice that had been treated with AAV4-GFP indicated that GFP was distributed throughout the ependymal cell layer of the ventricular system. For example, GFP was visualized in the anterior lateral ventricles, the lateral ventricles, the third ventricle, and the fourth ventricle (FIG. 1). GFP was also visualized in the choroid plexus of the ventricular system and the ependymal cell layer of the spinal cord central canal (including the cervical, thoracic, and lumbar regions) (FIG. 2).

Intracerebroventricular injection of recombinant AAV encoding glucocerebrosidase in a neuronopathic mouse model of Gaucher disease There are animal models of Gaucher disease, which are derived by targeted disruption of the corresponding mouse gene. For example, there are models of acute neuronopathic Gaucher disease developed by Enquist et al. 2007 PNAS 104(44): 17483-17488 (incorporated herein by reference in its entirety). These mice exhibit close similarity, in both pathological findings and clinical manifestations, to human patients with severe neuronopathic Gaucher disease. An experiment was performed in one of the two models, the K14-lnl/lnl (also referred to herein as the "K2" mouse). The K2 model is the more severe form of the models described in Enquist et al. as the mouse manifests with a more rapid clinical and pathological progression of symptoms.

At one day post-birth, neonatal K2 mice were injected bilaterally using intracerebroventricular injection into the lateral ventricles with a recombinant adeno-associated virus encoding for human glucocerebrosidase (GC) at a dose of 1.2 e10 genome copies total per brain delivered in a volume of 2 microliters per lateral ventricle. The AAV virus comprised an AAV5 capsid, AAV2 ITRs, and encoded for human GC (AAV-GC). The K2 mice have disruptions in both copies of the GC gene and should have no endogenous expression of GC in their tissues. At one day post-birth, two control groups of littermates of the K2 mice were also injected with the virus. The first control group contained the "wild-type" mouse group, which have no disruptions in the GC gene and thus normal, endogenous GC expression. The second control group contained the "heterozygote" mouse group, which have one disrupted copy of the GC gene and one non-disrupted copy of the GC gene and thus express some endogenous level of GC.

The groups of mice were evaluated for total GC enzymatic activity in the brain and the liver as a representative peripheral organ; reversal of pathology; weight as surrogate for overall health; extension of lifespan via a Kaplan-Meier survival curve; and spread of enzyme within the central nervous system. To determine mortality in a reliable and humane fashion, an artificial end point is used as defined by when end-stage paralysis in mice was observed.

Figure 3:
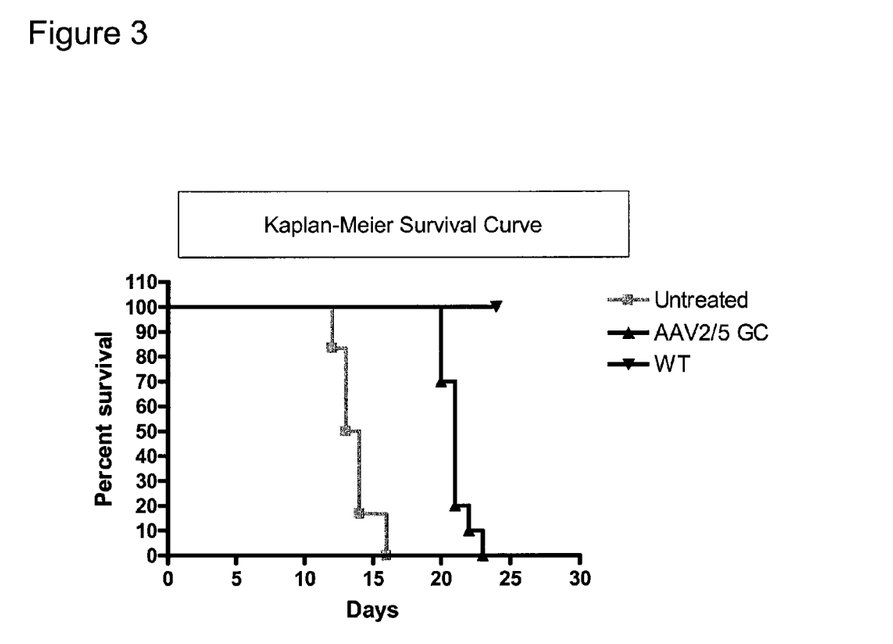
FIG. 3 is a Kaplan-Meier survival curve demonstrating the survival data of the AAV-GC treated K2 mice (AAV2/5 GC; represented by triangles) and the AAV-GC treated wild-type littermate control group (WT; represented by upside-down triangles). Historical survival data from the K2 mice in the mouse colony has been added to the Kaplan-Meier survival curve (Untreated; represented by boxes). The difference between the historical median survival time of untreated K2 mice and the AAV-GC treated K2 mice median survival time is statistically significant ($p<0.0001$).

FIG. 3 is a Kaplan-Meier survival curve demonstrating the survival data of the AAV-GC treated K2 mice (AAV2/5 GC; represented by triangles) and the AAV-GC treated wild-type littermate control group (WT; represented by upside-down triangles). Historical survival data from the K2 mice in the mouse colony has been added to the Kaplan-Meier survival curve (Untreated; represented by boxes). As indicated by the survival data, the AAV-GC treated K2 mice have a significantly longer median survival time (median survival=21 days) as compared to the historical median survival time for the untreated K2 mice (median survival=13.5 days). The difference between the historical median survival time and the AAV-GC treated K2 mice median survival time is statistically significant (p<0.0001). The AAV-GC wild-type littermate control group survived until the termination of the study. The AAV-GC treated heterozygote littermate control group also survived until the termination of the study (data not shown on figure).

Figure 4:
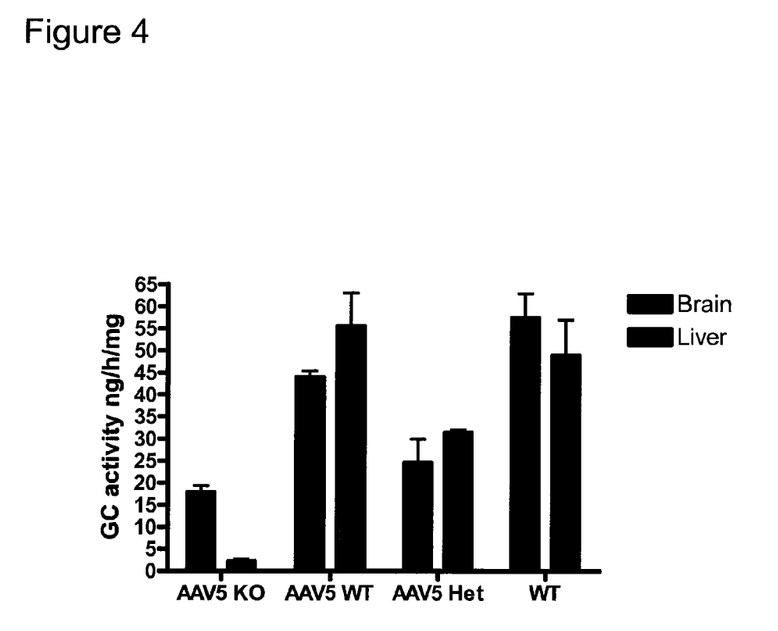
FIG. 4 presents GC activity in the brain and liver of AAV-GC treated K2 mice (injected as described above) as compared to several control groups. The first control group contained the "wild-type" mouse group, which have no disruptions in the GC gene and thus normal, endogenous GC expression. This group was treated with AAV-GC in the same manner as the treated K2 mice (labeled AAV5 WT in FIG. 4). The second control group contained the "heterozygote" mouse group, which have one disrupted copy of the GC gene and one non-disrupted copy of the GC gene and thus express some endogenous level of GC. These mice were also treated with AAV-GC (labeled AAV5 Het in FIG. 4). The final control group also contained the "wild-type" mouse group, but these mice were not treated with AAV-GC (labeled WT in FIG. 4).

FIG. 4 represents GC activity in the brain and liver of AAV-GC treated K2 mice (injected as described above) as compared to several control groups. The first control group contained the "wild-type" mouse group, which have no disruptions in the GC gene and thus normal, endogenous levels of GC expression. This group was treated with AAV-GC in the same manner as the treated K2 mice (labeled AAV5 WT in FIG. 4). The second control group contained the "heterozygote" mouse group, which have one disrupted copy of the GC gene and one non-disrupted copy of the GC gene and thus express some level of endogenous GC. These mice were also treated with AAV-GC (labeled AAV5 Het in FIG. 4). The final control group also contained the "wild-type" mouse group, but these mice were not treated with AAV-GC (labeled WT in FIG. 4). As demonstrated in FIG. 4, intracerebroventricular injection of AAV encoding for GC resulted in GC enzyme activity in the brain of K2 mice. In these treated K2 mice, GC activity in the liver was not significantly above background.

Figure 5:
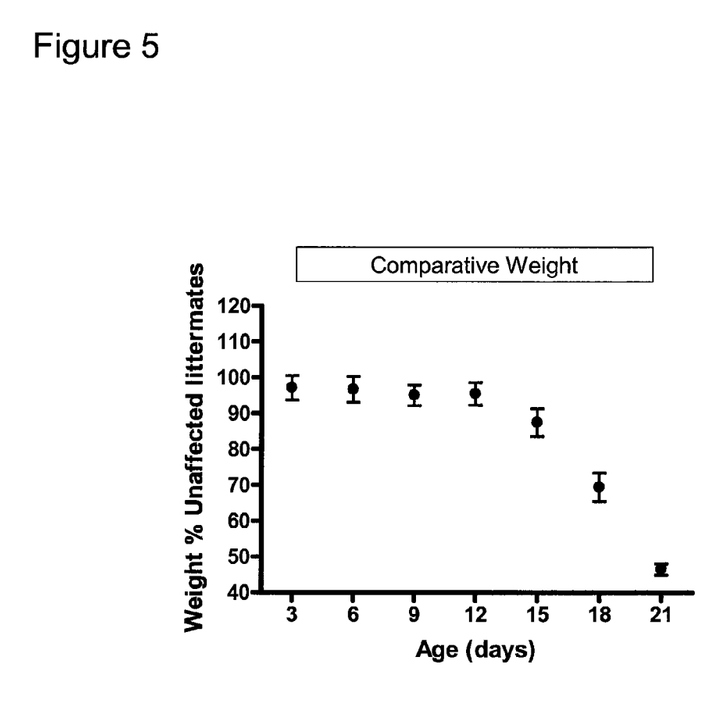
FIG. 5 represents the growth of AAV-GC treated K2 mice over time (as measured by weight) as compared to the growth over time of AAV-GC treated wild-type littermates. In this mouse model and regardless of genotype, the mouse pups from smaller litters tend to be larger than the mouse pups from larger litters. To account for this variation in mouse pup size as a function of the litter size, the weight of the K2 mouse pups are normalized as a percentage of their own littermates.

FIG. 5 represents the growth of AAV-GC treated K2 mice over time (as measured by weight) as compared to the growth over time of AAV-GC treated wild-type littermates. In this mouse model and regardless of genotype, the mouse pups from smaller litters tend to be larger than the mouse pups from larger litters. To account for this variation in mouse pup size as a function of the litter size, the weight of the K2 mouse pups are normalized as a percentage of their own littermates. There is no significant difference between the growth over time of the K2 mice as compared to the heterozygote littermates (data not shown). In theory, the weight curve for untreated K2 mice should be different than the curve of the AAV-GC treated K2 mice represented by FIG. 5. Based on the historical survival data from the K2 colony, the untreated K2's are dead around 12-15 days post-birth, which is when the AAV-GC treated K2 animals start losing weight.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

References

1. Lindsay, R. M. Neurotrophic growth factors and neurodegenerative diseases: therapeutic potential of the neurotrophins and ciliary neurotrophic factor. *Neurobiol Aging* 15, 249-51 (1994).
14. Matsushita, M. Projections from the lowest lumbar and sacral-caudal segments to the cerebellar nuclei in the rat, studied by anterograde axonal tracing. *J Comp Neurol* 404, 21-32 (1999).
17. Matsushita, M. & Gao, X. Projections from the thoracic cord to the cerebellar nuclei in the rat, studied by anterograde axonal tracing. *J Comp Neurol* 386, 409-21 (1997).
18. Matsushita, M. & Xiong, G. Projections from the cervical enlargement to the cerebellar nuclei in the rat, studied by anterograde axonal tracing. *J Comp Neurol* 377, 251-61 (1997).
19. Matsushita, M. & Yaginuma, H. Afferents to the cerebellar nuclei from the cervical enlargement in the rat, as demonstrated with the *Phaseolus vulgaris* leucoagglutinin method. *Neurosci Lett* 113, 253-9 (1990).
20. Matsushita, M. & Yaginuma, H. Projections from the central cervical nucleus to the cerebellar nuclei in the rat, studied by anterograde axonal tracing. *J Comp Neurol* 353, 234-46 (1995).
21. Voogd, J. The cerebellar nuclei and their efferent pathways. in *The rat nervous system* (ed. Paxinos, G.) 208-215 (Elsevier Academic Press, San Diego, 2004).
22. Dodge, J. C. et al. Gene transfer of human acid sphingomyelinase corrects neuropathology and motor deficits in a mouse model of Niemann-Pick type A disease. *Proc Natl Acad Sci USA* 102, 17822-7 (2005).
23. Kasarskis, E. J. et al. A controlled trial of recombinant methionyl human BDNF in ALS: The BDNF Study Group (Phase III). *Neurology* 52, 1427-33 (1999).
26. Chirmule, N. et al. Immune responses to adenovirus and adeno-associated virus in humans. *Gene Ther* 6, 1574-83 (1999).
37. High, K. A. Clinical gene transfer studies for hemophilia B. *Semin Thromb Hemost* 30, 257-67 (2004).
38. Maheshri, N., Koerber, J. T., Kaspar, B. K. & Schaffer, D. V. Directed evolution of adeno-associated virus yields enhanced gene delivery vectors. *Nat Biotechnol* 24, 198-204 (2006).
40. Confavreux C, Hutchinson M, Hours M M, Cortinovis-Tourniaire P, Moreau T. Rate of pregnancy-related relapse in multiple sclerosis. Pregnancy in Multiple Sclerosis Group. N Engl J. Med. 1998 Jul. 30; 339(5):285-91.
42. Gensert J M, Goldman J E (1997) Endogenous progenitors remyelinate demyelinated axons in the adult CNS. Neuron 19:197-203.
43. Gregg C, Shikar V, Larsen P, Mak G, Chojnacki A, Yong V W, Weiss S. White matter plasticity and enhanced remyelination in the maternal CNS. J. Neurosci. 2007 Feb. 21; 27(8): 1812-23.
44. Handwerger S, Freemark M. The roles of placental growth hormone and placental lactogen in the regulation of human fetal growth and development. J Pediatr Endocrinol Metab. 2000 April; 13(4):343-56.
45. Lesniak M A, Gorden P, Roth J. Reactivity of non-primate growth hormones and prolactins with human growth hormone receptors on cultured human lymphocytes. Clin Endocrinol Metab. 1977 May; 44(5):838-49.
46. Levison S W, Young G M, Goldman J E (1999) Cycling cells in the adult rat neocortex preferentially generate oligodendroglia. J Neurosci Res 57:435-446.
47. Menn B, Garcia-Verdugo J M, Yaschine C, Gonzalez-Perez O, Rowitch D, Alvarez-Buylla A (2006) Origin of oligodendrocytes in the subventricular zone of the adult brain. J Neurosci 26:7907-7918.
48. Pelton E W, Grindeland R E, Young E, Bass N H. Effects of immunologically induced growth hormone deficiency on myelinogenesis in developing rat cerebrum. Neurology. 1977 March; 27(3):282-8.
49. Peters A, Sethares C (2004) Oligodendrocytes, their progenitors and other neuroglial cells in the aging primate cerebral cortex. Cereb Cortex 14:995-1007.
50. Polito A, Reynolds R (2005) NG2-expressing cells as oligodendrocyte progenitors in the normal and demyelinated adult central nervous system. J Anat 207:707-716.
51. Selenkow H A, Saxena B N, Dana C L. Measurement and pathophysiologic significance of human placental lactogen. In Pecile A, Finzi C (eds). The Feto-Placental Unit. Amersterdam, Excerpta Medica, 1969, p340.
52. van Walderveen M A, Tas M W, Barkhof F, Polman C H, Frequin S T, Hommes O R, Valk J (1994) Magnetic resonance evaluation of disease activity during pregnancy in multiple sclerosis. Neurology 44:327-329.
53. Voskuhl R R (2003) Hormone-based therapies in MS. Int MS J 10:60-66.
54. Zumkeller W. Current topic: the role of growth hormone and insulin-like growth factors for placental growth and development. Placenta. 2000 July-August; 21(5-6):451-67.
55. Belichenko P V, Dickson P I, Passage M, Jungles S, Mobley W C, Kakkis E D. Penetration, diffusion, and uptake of recombinant human alpha-1-iduronidase after intraventricular injection into the rat brain. Mol Genet Metab. 2005; 86(1-2):141-9.
56. Kakkis E, McEntee M, Vogler C, Le S, Levy B, Belichenko P, Mobley W, Dickson P, Hanson S, Passage M. Intrathecal enzyme replacement therapy reduces lysosomal storage in the brain and meninges of the canine model of MPS I. Mol Genet Metab. 2004; 83(1-2):163-74.
57. Bembi B, Clana G, Zanatta M, et al. Cerebrospinal-fluid infusion of alglucerase in the treatment for acute neuronopathic Gaucher's disease. Pediatr Res 1995; 38:A425.
58. Lonser R R, Walbridge S, Murray G J, Aizenberg M R, Vortmeyer A O, Aerts J M, Brady R O, Oldfield E H. Convection perfusion of glucocerebrosidase for neuronopathic Gaucher's disease. Ann Neurol. 2005 April; 57(4): 542-8.

The disclosure of each reference cited is expressly incorporated herein.

We claim:

1. A method to deliver acid beta glucosidase to the central nervous system in a subject having Gaucher disease, comprising:
   administering a recombinant AAV4 or AAV5 viral vector comprising a transgene encoding acid beta glucosidase to at least one ventricle of the brain selected from the group consisting of a lateral ventricle and the fourth ventricle by intraventricular administration, whereby said transgene is expressed and acid beta glucosidase is delivered to the central nervous system, wherein the subject is a mammal.

2. The method of claim 1, wherein the viral vector is administered by direct injection into the lateral ventricle of the brain.

The following is an examiner's statement of reasons for allowance: The art does not teach or suggest a method to deliver acid beta glucosidase to the central nervous system in a subject having Gaucher disease, comprising: administering a recombinant AAV4 or AAV5 viral vector comprising a transgene encoding acid beta glucosidase to at least one ventricle of the brain selected from the group consisting of a lateral ventricle and the fourth ventricle by intraventricular administration, whereby said transgene is expressed and acid beta glucosidase is delivered to the central nervous system, wherein the subject is a mammal.

3. The method of claim 1 wherein the viral vector is administered by direct injection into the fourth ventricle of the brain.

4. The method of claim 1 wherein said mammal is selected from the group consisting of a rodent, a murine, a simian, and a human.

5. The method of claim 1 wherein said subject is a human patient.

6. The method of claim 1, wherein the AAV5 viral vector comprises the AAV5 capsid.

7. The method of claim 1 wherein the AAV5 viral vector comprises the AAV4 capsid.

* * * * *